United States Patent
Rahman et al.

(10) Patent No.: US 7,319,029 B2
(45) Date of Patent: Jan. 15, 2008

(54) **LIPASE FROM *GEOBACILLUS* SP. STRAIN T1**

(75) Inventors: Raja Noor Zaliha Abd. Rahman, Selangor (MY); Abu Bakar Salleh, Selangor (MY); Mahiran Basri, Selangor (MY); Leow Thean Chor, Selangor (MY)

(73) Assignee: Universiti Purta Malaysia, Selangor (MY)

( * ) Notice: Subject to any disclaimer, the term of this patent is extended or adjusted under 35 U.S.C. 154(b) by 0 days.

(21) Appl. No.: 11/193,282

(22) Filed: Jul. 29, 2005

(65) Prior Publication Data

US 2006/0024789 A1 Feb. 2, 2006

(30) Foreign Application Priority Data

Aug. 2, 2004 (MY) .............................. PI 20043110

(51) Int. Cl.
*C12N 1/20* (2006.01)
*C12Q 1/46* (2006.01)
*C12Q 9/74* (2006.01)

(52) U.S. Cl. ....................... 435/252.3; 435/19; 435/20; 435/198

(58) Field of Classification Search ...................... None
See application file for complete search history.

(56) References Cited

OTHER PUBLICATIONS

Gupta et al., Appl Microbiol Biotechnol. Jun. 2004;64(6):763-81. Epub Feb. 14, 2004.Bacterial lipases: an overview of production, purification and biochemical properties.*

Leow al., High Level of Thermostable Lipase from *Geobacillus* sp. Strain T1, Biosci Biotechnol Biochem. Jan. 2004;68(1):96-103).*
Amershambiosciences. Map of the glutathione S-transferase fusion vectors. Life Science News, Knaust et al., 2000 pp. 1-2.*
Frangioni, John V. et al., "Solubilization and Purification of Enzymatically Active Glutathione S-Transferase (pGEX) Fusion Proteins", *Analytical Biochemistry*, 1993, pp. 179-187, Molecular Medicine Unit, Beth Israel Hospital, Boston, Massachusetts.

* cited by examiner

*Primary Examiner*—Joseph Woitach
*Assistant Examiner*—Maria Leavitt
(74) *Attorney, Agent, or Firm*—Saliwanchik, Lloyd & Saliwanchik

(57) ABSTRACT

A biologically pure culture of *Geobacillus* Strain T1 bacteria isolated from Palm Oil Mill Effluent capable of producing thermostable lipase T1 gene. The production of thermostable lipase T1 gene from a novel *Geobacillus* bacterium having a designated as strain T1, was aerobic, gram positive and endospore-forming, rod-shaped. The G+C content of the genomic DNA was 52.6%. On the basic of physiological data, phenotypic traits and molecular analysis, strain T1 represents a novel species within the genus *Geobacillus*, The thermostable T1 lipase gene was subcloned into the pGEX-4T1 vector with and without signal peptide in prokaryotic system. The 28 amino acid residues signal peptide alter the conformation of GST moiety and preventing it from bind to affinity glutathione Sepharose column. By expression and simplification of the purification through single step affinity chromatography shows a specific activity of 292.929 U/mg and 72.55% of fusion lipase was recovered from crude cell lysate. T1 mature lipase was successfully purified with a final recovery of 51.49% and specificity activity of 959.033 U/mg.

9 Claims, 8 Drawing Sheets

Effect of inhibitors on lipase activity.

SEQUENCE LISTING

<160> NUMBER OF SEQ ID NOS: 4

<210> SEQ ID NO 1
<211> LENGTH: 1519
<212> TYPE: DNA
<213> ORGANISM: Geobacillus sp. T1

<400> SEQUENCE: 1

```
gagtttgatc ctggctcagg acgaacgctg gcggcgtgcc taatacatgc aagtcgagcg         60
gaccggatcg gagcttgctc tgatttggtc agcggcggac gggtgagtaa cacgtgggca        120
acctgcccgc aagaccggga taactccggg aaaccggagc taataccgga taacaccgaa        180
gaccgcatgg tctttggttg aaaggcggcc tttggctgtc acttgcggat gggcccgcgg        240
cgcattagct agttggtgag gtaacggctc accaaggcga cgatgcgtag ccggcctgag        300
agggtgaccg gccacactgg gactgagaca cggcccagac tcctacggga ggcagcagta        360
gggaatcttc cgcaatgggc gaaagcctga cggagcgacg ccgcgtgagc gaagaaggcc        420
ttcgggtcgt aaagctctgt tgtgagggac gaaggagcgc cgttcgaaga gggcggcgcg        480
gtgacggtac ctcacgagga agccccggct aactacgtgc cagcagccgc ggtaatacgt        540
aggggcgag cgttgtccgg aattattggg cgtaaagcgc gcgcaggcgg ttccttaagt         600
ctgatgtgaa agcccacggc tcaaccgtgg agggtcattg gaaactgggg acttgagtg         660
caggagagga gagcggaatt ccacgtgtag cggtgaaatg cgtagagatg tggaggaaca        720
ccagtggcga aggcggctct ctggcctgca actgacgctg aggcgcgaaa gcgtggggag        780
caaacaggat tagataccct ggtagtccac gccgtaaacg atgagtgcta agtgttagag        840
gggtcacacc ctttagtgct gcagctaacg cgataagcac tccgccgggg gagtacggcc        900
gcaaggctga aactcaaagg aattgacggg gcccgcaca agcggtggag catgtggttt         960
aattcgaagc aacgcgaaga accttaccag gtcttgacat cccctgacaa cccaagagat       1020
tgggcgttcc cccttcgggg gacagggtg acaggtggtg catggttgtc gtcagctcgt        1080
gtcgtgagat gttgggttaa gtcccgcaac gagcgcaacc ctcgcctcta gttgccagca       1140
cgaaggtggg cactctagag ggactgccgc cgacaagtcg gaggaaggtg gggatgacgt       1200
caaatcatca tgccccttat gacctgggct acacacgtgc tacaatgggc ggtacaaagg       1260
gctgcgaacc cgcgaggggg agcgaatccc aaaaagccgc tctcagttcg gattgcaggc       1320
tgcaactcgc ctgcatgaag ccggaatcgc tagtaatcgc ggatcagcat gccgcggtga       1380
atacgttccc gggccttgta cacaccgccc gtcacaccac gagagcttgc aacacccgaa       1440
gtcggtgagg caacccgcaa gggagccagc cgccgaaggt ggggcaagtg attggggtga       1500
agtcgtaaca aggtagccg                                                    1519
```

<210> SEQ ID NO 2
<211> LENGTH: 34
<212> TYPE: DNA
<213> ORGANISM: Artificial Sequence
<220> FEATURE:
<223> OTHER INFORMATION: Forward primer pGEX-For

<400> SEQUENCE: 2

```
gaagggatcc gtgatgaaat gctgtcggat tatg                                      34
```

<210> SEQ ID NO 3
<211> LENGTH: 31

```
<212> TYPE: DNA
<213> ORGANISM: Artificial Sequence
<220> FEATURE:
<223> OTHER INFORMATION: Reverse primer pGEX-Rev

<400> SEQUENCE: 3
aatagaattc ttaaggctgc aagctcgcca a                              31

<210> SEQ ID NO 4
<211> LENGTH: 31
<212> TYPE: DNA
<213> ORGANISM: Artificial Sequence
<220> FEATURE:
<223> OTHER INFORMATION: Forward primer EH2-F

<400> SEQUENCE: 4
gacgggatcc gcatccctac gcgccaatga t                              31
```

LIPASE FROM *GEOBACILLUS* SP. STRAIN T1

CROSS-REFERENCE TO A RELATED APPLICATION

The subject application claims priority to Malaysian Application No. PI 2004 3110, filed Aug. 2, 2004.

FIELD OF INVENTION

This invention relates to a novel microorganism and a production method. More particularly, to a novel microorganism which produces a thermostable lipase T1.

BACKGROUND OF THE INVENTION

Lipase is a very important metabolic enzyme for ordinary biological body; it can hydrolyze fat to produce free fatty acid. Lipases or acylglycerol hydrolases are enzymes that catalyze the hydrolysis of long chain triglyceride into diacylglyceride, monoglyceride, glycerol and free fatty acids. However, lipases are also capable of catalyzing the reverse reaction of hydrolysis in the formation of esters from alcohols and fatty acids or via transesterification.

The lipase is extensively used as an enzyme for food processing to flavor dairy products, medicines as digestive, improvements of fats and oils, and the like. The lipase is required to have various characteristics for each use, and a thermostable lipase is applied to a wide various characteristics for each use, and a thermostable lipase is applied to a wide variety of fields and requested to be variously used.

Microbial extracellular lipases are usually more thermostable than animals or plants lipases. Microbial extracellular lipase has a potential use in industries and diagnostics. A major requirement for commercial enzyme is thermal stability because thermal denaturation is a common cause of enzyme inactivation. In addition, increasing enzyme thermostability would allow enzymatic reactions to be carried out at higher temperatures; this would help to increase conversion rates, substrate solubility and to reduce the possibility of microbial growth and the viscosity of the reaction medium.

Although thermophiles could be a good candidate in producing thermostable enzyme, but it is often impractical because of low yield and also high temperature fermentation equipment may be needed. To overcome this problem, a molecular approach through genetic engineering becomes a good alternative to achieve high-level expression towards bulk production economically via prokaryotic system. So far, several thermostable lipases have been successfully cloned and expressed in heterologous hosts intracellularly.

For fundamental studies and for commercial purposes expression of foreign protein in prokaryotic systems is most widely used to achieve high-level expression. Expression vector and host are an important issue for achieving maximal expression of cloned gene, however molecular cloning of foreign gene does not ensure that the gene been expressed successfully.

At this present invention, rapid cloning of thermostable lipase through Polymerase Chain Reaction (PCR) technique and manipulation of the thermostable lipase T1 gene is express through prokaryotic system using various kinds of promoters.

SUMMARY OF THE INVENTION

The bacterium strain *Geobacillus* sp. Strain T1 (DSMZ Deposit No. *Geobacillus* sp. T1-DSM 17139) of the present invention provides a thermostable T1 lipase gene and a method of producing it. The present invention also provides a transformant having a recombinant host cell expressing the thermostable T1 lipase gene and a method preparing.

BRIEF DESCRIPTION OF THE SEQUENCES

Figure 1:
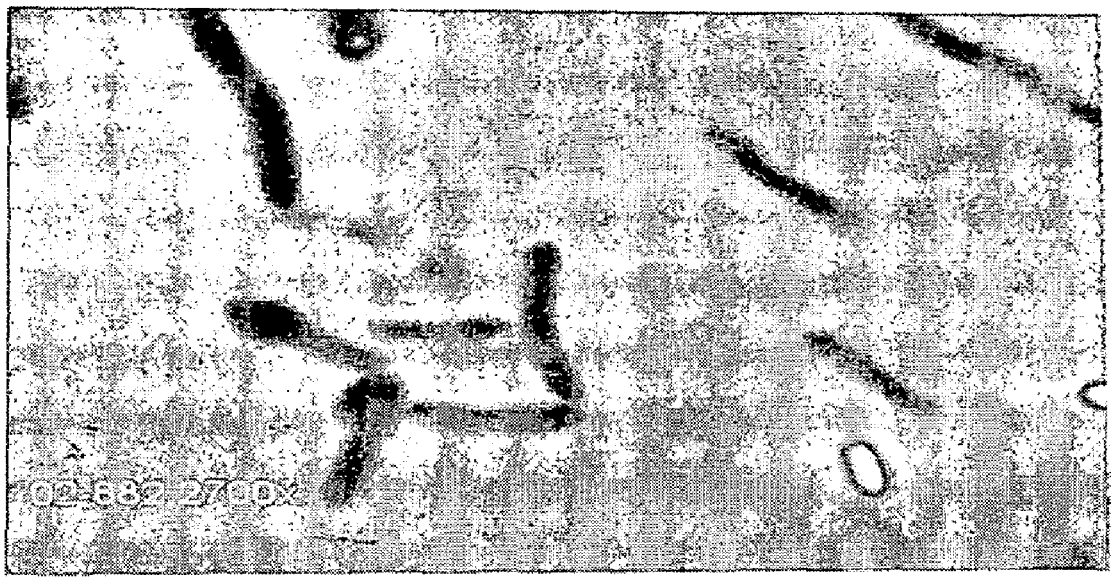
FIG. 1 is a diagram showing the micrograph of strain T1.

SEQ ID NO:1 is the complete 16S rDNA sequence of 1519 bp (AY166603).
SEQ ID NO:2 is forward primers pGEX-For.
SEQ ID NO:3 is reverse primers pGEX-Rev.
SEQ ID NO:4 is forward primer EH2-F.

DETAILED DESCRIPTION OF THE INVENTION

Screening of *Geobacillus* sp. Strain T1

According to the present invention, *Geobacillus* sp. Strain T1 was isolated and identified based on thermophilic species. The *Geobacillus* sp. Strain T1 culture could be obtained from Enzyme and Microbial Technology Research Department of Biochemistry and Microbiology, Faculty of Science and Environmantal Studies, University Putra Malaysia.

In the process of screening for lipase producing bacterium from Palm Oil Mill Effluent in Malaysia, isolate T1 which gave positive result on Triolein agar plate was isolated. To verify the systematic position of this lipase-producing bacterium, a study of morphological and physiological characteristics, 16S rRNA analysis, cellular fatty acids analysis, DNA composition, DNA/DNA hybridization and RiboPrint analysis were undertaken.

Isolation and Identification of *Geobacillus* sp. Strain T1

Samples were taken from a Palm Oil Mill Effluent in Selangor, Malaysia. *Geobacillus* sp. Strain T1 was isolated from an enriched medium (pH 7.0) containing NaCl 0.2%, $MgSO_4.7H_2O$ 0.04%, $MgCl_2.6H_2O$ 0.07%, $CaCl_2.2H_2O$ 0.05%, $KH_2PO_4$ 0.03%, $K_2HPO_4$ 0.03%, $(NH_4)_2SO_4$ 0.05% with the sole carbon source of Olive oil (2%) at 60° C. under shaking condition of 150 rpm. It was plated on Triolein agar plate form screening of lipase producer.

For morphological studies, pure bacterial strain was streaked on nutrient agar plate and incubated at 60° C. prior to gram staining, the results were then observed under light microscope. Morphological and physiological characteristics were sent to DSMZ (Deutsche Sammlung von Mikroorganismen und Zellkulturen) (German Collection of Microorganism and Cell Cultures). The physiological characteristics study includes catalase and oxidase test, anaerobic growth, Voges-Proskauer test, growth at 30° C., 40° C. and 70° C., growth in medium with pH 5.7, NaCl 2%, 5% and lysozyme broth, fermentation of D-glucose, L-arabinose, D-xylose, D-mannitol and D-glucose, hydrolysis of starch, gelatin, casein and tween 80, decomposition of tyrosine, use of citrate and propionate, nitrate reduction, indol production, phenylalanine deaminase and arginine dihydrolase test were conducted. Fatty acids were extracted and analysed following the instructions of Sherlock microbial identification system.

16S rDNA was amplified by PCR using two universal primers and the PCR product was purified. A purified PCR product was cloned into TOPO TA PCR 2.1 cloning vector (Invitrogen). The recombinant plasmid was extracted and was then sequenced using an ABI PRISM 377 DNA sequencer (Applied Biosystems).

A chromosomal DNA was isolated and purified and G+C content was determined by using chromatography conditions. The DNA was hydrolyzed and the resultant nucleotides were analyzed by reverse-phase HPLC. DNA/DNA hybridization was carried out with the using a model 2600 spectrophotometer.

A standardized, automated ribotyping was performed using the Qualicon™ RiboPrinter system. The RiboPrinter system combines molecular processing steps for ribotyping in a stand-alone, automated instrument. Steps including cell lysis, digestion of chromosomal DNA with restriction enzyme EcoR1, separation of fragments by electrophoresis, transfer of DNA fragments to a nylon membrane, hybridization to a probe generated from the rrnB operon from *E. coli*, chemiluminescent detection of the probe to the fragments containing rrn operon sequences, image detection and computerized analysis of RiboPrint patterns.

The isolated Strain T1 was aerobic, gram positive, endospore forming, rod-shaped bacteria (0.8-1.0 μm width and 2.5-6.0 μm long) (FIG. 1). The DNA base composition of strain T1 was around 52.6% mol G+C. The cylindrical endospores were appeared terminally in swollen sporangia. The growth of strain T1 occurred even at 70° C. but no growth observed at 30° C. and 40° C. It was tolerant with the presence of NaCl up to 2%. Acid was produced from D-fructose, but not from D-glucose and D-mannitol. It showed positive result in citrate and nitrate test. The morphological and physiological characteristics are presented in Table 1 and 2.

TABLE 1

Morphological and physiological properties of *Geobacillus* strain T1.

| Characteristic | *Geobacillus* strain T1 |
|---|---|
| Cell width (μm) | 0.8-1.0 |
| Cell length (μm) | 2.5-6.0 |
| Spores oval/cylindrical | + |
| Swollen sporangium | d |
| Catalase | + |
| Oxidase | – |
| Anaerobic growth | – |
| VP reaction | – |
| pH in VP broth | 4.9 |
| Growth at 30° C. | – |
| 40° C. | – |
| 70° C. | + |
| Growth in | |
| Medium pH 5.7 | + |
| NaCl 2% | + |
| 5% | – |
| Lysozyme broth | – |
| Production of acid from: | |
| D-glucose | – |
| L-arabinose | w |

TABLE 1-continued

Morphological and physiological properties of *Geobacillus* strain T1.

| Characteristic | *Geobacillus* strain T1 |
|---|---|
| D-xylose | w |
| D-mannitol | – |
| D-fructose | + |
| Gas from glucose | – |
| Lecithinase | n.g. |
| Hydrolysis of: | |
| Starch | + |
| Gelatin | – |
| Casein | – |
| Tween 80 | – |
| Decomposition of tyrosine | + |
| Use of: | |
| Citrate | + |
| Propionate | – |
| Nitrate reduction | + |
| Indole production | – |
| Phenylalanine deaminase | – |
| Arginine dihydrolase | – |

+—positive;
-—negative;
w—weak reaction;
n.d.—not determined;
n.g.—not growth.

TABLE 2

Comparison of biochemical, morphological and physiological properties of *Geobacillus* strain T1 and related thermophilic bacilli.

| Characteristic | 1 | 2 | 3 |
|---|---|---|---|
| G + C mol % of DNA | 52.6 | 53.7 | 51.0 |
| Growth at 30° C. | – | – | – |
| 70° C. | + | + | + |
| Spore shape | C | O | O/C |
| Position | T | T | T |
| Catalase | + | + | n.d. |
| Oxidase | – | + | – |
| Anaerobic growth | – | – | – |
| Acid from glucose | – | + | + |
| Formation of acetoin | – | – | – |
| Indole | – | – | – |
| $H_2S$ | – | n.d. | n.d. |
| Citrate utilization | + | – | + |
| Hydrolysis of: | | | |
| Starch | + | + | + |
| Gelatin | – | n.d. | + |
| Casein | – | w | – |
| Nitrate reduction | + | n.d. | + |

+—positive;
-—negative;
w—weak reaction;
n.d.—not determined;
C—cylindrical;
O—oval;
T—terminal.
Taxa are indicated as: 1, *Geobacillus zalihaii*; 2, *Geobacillus thermoleovorans* (Zarilla and Perry, 1986); 3, *Geobacillus kaustophilus* (White et al., 1993).

A complete 16S rDNA sequence of 1519 bp (AY166603) is determined as below (SEQ ID NO: 1).

```
   1 gagtttgatc ctggctcagg acgaacgctg gcggcgtgcc taatacatgc aagtcgagcg 61 gaccggatcg gagcttgctc tgatttggtc agcggcggac gggtgagtaa cacgtgggca 121 acctgcccgc aagaccggga taactccggg aaaccggagc taataccgga taacaccgaa 181 gaccgcatgg tctttggttg aaaggcggcc tttggctgtc acttgcggat gggcccgcgg 241 cgcattagct agttggtgag gtaacggctc accaaggcga cgatgcgtag ccggcctgag 301 agggtgaccg gccacactgg gactgagaca cggcccagac tcctacggga ggcagcagta 361 gggaatcttc cgcaatgggc gaaagcctga cggagcgacg ccgcgtgagc gaagaaggcc 421 ttcgggtcgt aaagctctgt tgtgagggac gaaggagcgc cgttcgaaga gggcggcgcg 481 gtgacggtac ctcacgagga agccccggct aactacgtgc cagcagccgc ggtaatacgt 541 aggggcgag cgttgtccgg aattattggg cgtaaagcgc gcgcaggcgg ttccttaagt 601 ctgatgtgaa agcccacggc tcaaccgtgg agggtcattg gaaactgggg gacttgagtg 661 caggagagga gagcggaatt ccacgtgtag cggtgaaatg cgtagagatg tggaggaaca 721 ccagtggcga aggcggctct ctggcctgca actgacgctg aggcgcgaaa gcgtggggag 781 caaacaggat tagataccct ggtagtccac gccgtaaacg atgagtgcta agtgttagag 841 gggtcacacc ctttagtgct gcagctaacg cgataagcac tccgccgggg gagtacggcc 901 gcaaggctga aactcaaagg aattgacggg ggcccgcaca agcggtggag catgtggttt 961 aattcgaagc aacgcgaaga accttaccag gtcttgacat cccctgacaa cccaagagat 1021 tgggcgttcc cccttcgggg ggacagggtg acaggtggtg catggttgtc gtcagctcgt 1081 gtcgtgagat gttgggttaa gtcccgcaac gagcgcaacc ctcgcctcta gttgccagca 1141 cgaaggtggg cactctagag ggactgccgg cgacaagtcg gaggaaggtg gggatgacgt 1201 caaatcatca tgccccttat gacctgggct acacacgtgc tacaatgggc ggtacaaagg 1261 gctgcgaacc cgcgaggggg agcgaatccc aaaaagccgc tctcagttcg gattgcaggc 1321 tgcaactcgc ctgcatgaag ccggaatcgc tagtaatcgc ggatcagcat gccgcggtga 1381 atacgttccc gggccttgta cacaccgccc gtcacaccac gagagcttgc aacacccgaa 1441 gtcggtgagg caacccgcaa gggagccagc cgccgaaggt ggggcaagtg attggggtga 1501 agtcgtaaca aggtagccg
```

The major amount of cellular fatty acids of strain T1 was iso-fatty acids (Table 3). Among them, iso-branched pentadecanoic acid (iso-C15), hexadecanoic acid (iso-C16) and heptadecanoic acid (iso-C17) making up 78.33% of the total fatty acids especially iso-C15 and iso-C17 were in abundant. The fatty acid profile distinguishes the genus *Geobacillus* clearly from other mesophiles and thermophiles of the genera *Bacillus Alicyclobacillus, Brevibacillus, Aneurinibacillus, Sulfobacillus* and *Thermobacillus*. Although the strain T1 and *Geobacillus thermoleovorans* DSM 5366[T] shared typical fatty acid profile of *Bacillus* rRNA group 5 but it could be differentiated by % composition of iso-C 16 as indicated in Table 3.

TABLE 3

Cellular fatty acids composition of *Geobacillus* strain T1 and phylogenitical neighbor.

| Fatty acid | *Geobacillus* sp. strain T1 | *Geobacillus thermoleovorans* (DSM 5366[T]) |
|---|---|---|
| 10.0 | | 2.7 |
| 14.0 ISO | | 1.0 |
| 14:0 | 7.22 | 1.4 |
| 15:0 ISO | 32.42 | 22.6 |
| 15:0 ANTEISO | 1.01 | 1.3 |
| 15:0 | 0.82 | 2.1 |
| 16:0 ISO | 6.14 | 21.0 |
| 16:0 | 4.98 | 11.2 |

TABLE 3-continued

Cellular fatty acids composition of *Geobacillus* strain T1 and phylogenitical neighbor.

| Fatty acid | *Geobacillus* sp. strain T1 | *Geobacillus thermoleovorans* (DSM 5366$^T$) |
| --- | --- | --- |
| 17:0 ISO | 39.77 | 18.5 |
| 17:0 ANTEISO | 4.97 | 4.6 |
| 17:0 | 0.53 | 1.3 |
| 18:1 ISO H | 0.38 | |
| 18:0 ISO | 0.36 | 0.9 |
| 18:0 | 0.47 | 3.4 |
| 18.1 | | 1.2 |
| 19:0 ISO | 0.91 | |
| unsaturated C16 | | 6.6 |
| other | | 0.2 |

DNA/DNA hybridization study was carried out to verify the taxonomic relationship between strain T1 and phylogenetical neighbors. The genomic DNA/DNA relatedness between strain T1 and type strains *Geobacillus kaustophilus* DSM 7263$^T$ and *Geobacillus thermoleovorans* DSM 5366$^T$ were 64.9 and 68.8, respectively (Table 4).

TABLE 4

Levels of DNA/DNA reassociation (%) among *Geobacillus* strain T1 and thermophilic bacilli.

| Organisms | *Geobacillus* strain T1 |
| --- | --- |
| *Geobacillus kaustophilus* DSM 7263$^T$ | 66.9; 62.9 (average = 64.9) |
| *Geobacillus thermoleovorans* DSM 5366$^T$ | 70.0; 67.6 (average = 68.8) |

The DNA/DNA reassociation values were fall below the threshold value of 70% DNA/DNA similarity for definition of species. The RiboPrint analysis was carried out for the decision on the affiliation of strain T1. However, the RiboPrint pattern of strain T1 was not identified by the Dupont identification library to give rise to the identification at the species level (>0.85). Its RiboPrint pattern showed the highest similarity to *Geobacillus kaustophilus* DSM 7263$^T$ (0.69). The similarity to the pattern of *Geobacillus therleovorans* DSM 5366$^T$ was somewhat lower (0.57). The patterns of *Geobacillus kaustophilus* DSM 7263$^T$ and *Geobacillus thermoleovorans* DSM 5366$^T$ show a binary similarity of 0.64.

As a consequence, the strain T1 merits recognition as a member of a novel species through morphology and physiological studies, cellular fatty acids composition, DNA composition, DNA/DNA hybridization and RiboPrint analysis. Therefore, we proposed the creation of a novel species, *Geobacillus zalihae* sp. nov., for strain T1$^T$. (za.li.'hae N.L. gen. n. zalihae of zaliha, in honour to the scientist from Universiti Putra Malaysia, who has contributed significantly to extremophiles). Cells are rod-shaped, 0.8-1.0 width and 2.5-6.0 length, gram positive bacteria. The terminal spores are cylindrical and swollen the sporangium. The DNA base composition of strain T1 was around 52.6% mol G+C. It contained major amount of iso-fatty acids with iso-C15, and iso-C17 were in abundant (77.19%). Growth is aerobic and still growth at 70° C. and tolerant up to 2% NaCl. It can not perform anaerobic growth. Catalase and nitrate test are positive. No acid from D-glucose and D-mannitol. It can utilize citrate. Starch is hydrolysed but not gelatin and casein.

Cloning and Sequencing of Thermostable Lipase Gene from *Geobacillus* sp. Strain T1

Bacterial Strains and Plasmids

Recombinant plasmid pBAD/T1 (Leow et al., 2004) carrying thermostable T1 lipase gene was used as source for subcloning. *E. coli* strains were grown in LB medium at 37° C. pRSET C (Invitrogen), pET22b(+) (Novagen) and pGEX-4T1 (Amersham Bioscience; United Kingdom, England) was used for subcloning and expression.

DNA Manipulation

The plasmid DNA was isolated with a QIAGEN miniprep spin kit (QIAGEN; Hilden, Germany) according to the manufacturer's instructions. The PCR product was purified with a GeneClean Kit (Qbiogene; Carlsbad, USA) as described by the supplier. Competent cells of *E. coli* were prepared by using a conventional CaCl$_2$.

Subcloning and Expression of the Thermostable T1 Lipase Gene.

Subcloning of the T1 lipase gene was done by designing a set of primers which incorporated restriction enzyme sites BamH1/EcoR1 which involved primers pGEX-For: 5'-GAA GGG ATC CGT GAT GAA ATG CTG TCG GAT TAT G-3(SEQ ID NO:2) and pGEX-Rev: 5'-AAT AGA ATT CTT AAG GCT GCA AGC TCG CCA A-3' (SEQ ID NO:3) for subcloning of open reading frame of T1 lipase and EH2-F: 5'-GAC GGG ATC CGC ATC CCT ACG CGC CAA TGA T-3' (SEQ ID NO:4) and pGEX-Rev: 5'-AAT AGA ATT CTT AAG GCT GCA AGC TCG CCA A-3' (SEQ ID NO:3) for subcloning of T1 mature lipase gene. The ligated plasmid was used to transform *E. coli* strains and screened with tributyrin LB agar plates with appropriate antibiotics. *E. coli* BL21(De3)plysS harboring recombinant plasmids were grown in 1 L blue cap bottles containing 200 ml of LB medium supplemented with 100 μg/ml ampicillin and 35 μg/ml chloramphenicol on a rotary shaker (200 rpm) at 37° C.

The recombinant clones with and without signal peptide were induced with 1 mM of isopropyl-β-D-thiogalactopyranoside (IPTG) at OD$_{600}$ nm ~0.5 for different induction periods (0, 4, 8, 12, 20, 28, 36 and 44 h). It was further optimized by varying the concentration of IPTG (w/o, 0.025, 0.05, 0.1, 0.5, 1.0, 1.5 and 2.0 mM) and induction OD$_{600\ nm}$ (0.25, 0.50, 0.75 and 1.00). Cultures (10 ml) were harvested by centrifugation and resuspended with 2 ml of 50 mM of potassium phosphate buffer (pH 7.0) before sonication (Branson 250 sonifier: output 2, duty cycle 30 and min 2) and cleared by centrifugation (12,000 rpm, 20 min). The clear crude lysate was used for lipase assay.

Electrophoresis

SDS-PAGE was done on 12% of gel was used to analyse the protein. A broad range of protein standard (MBI Fermentas; St. Leon-Rot, Germany) was used as a molecular mass marker.

Purification of T1 Lipase

Four hundred mL of recombinant culture was harvested by centrifugation and concentrated to 40 mL prior to sonication. The crude cell lysate was loaded on a glutathione-Sepharose HP column (XK 16/20) containing 10 mL column volume equilibrated with PBS (pH 7.3) at a flow rate of 0.2 mL/minute. The column was washed with the same buffer until no protein was detected. The bound lipase was eluted with thrombin cleavage buffer (20 mM Tris-HCl, 100 mL NaCl and 0.33 mM CaCl2, pH 8.4 supplemented with 10 mM reduced glutathione. The fusion protein was subjected to thrombin cleavage at 20° C. for 20 h and buffer exchanged with Sephadex G-25 prior to dialysis against PBS (pH 7.3). The GST tag and thrombin enzyme were further removed by using Glutahione-Sepharose HP, HiTrap Glutathione 4FF and HiTrap Benzamidine in series.

Expression of T1 lipase including signal peptide was achieved through prokaryotic system involving pBAD, pRSET C, pET22b(+) and pGEX-4T1 which under the control of araC, T7, T7 lac and tac promoters. Among them, relatively higher level of expression was achieved with pGEX-4T1 expression system which under the control of tac promoter for inducible high level expression. It was chosen for further study. Simple optimization was carried out to increase the soluble protein of recombinant clone harboring recombinant plasmid pGEX-4T1 with signal peptide. A total of 11,708 U of lipase activity was detected when induced with 0.05 mM of IPTG at $OD_{600nm}$ ~0.5 for 8 hour which corresponded to a specific activity of 30.192 U/mg. (Table 5).

TABLE 5

Expression of T1 lipase gene with and without signal peptide.

| Optimization condition | Total activity from 1L culture (U) | |
|---|---|---|
| | Signal peptide | Without signal peptide |
| Induction time (h) | 5,627 (8) | 23,915 (12) |
| Inducer concentration (mM) | 11,708 (0.050) | 31,609 (0.025) |
| Induction $OD_{600\ nm}$ | — | 41,902 (0.750) |

Note:
The host BL21(De3)plysS harboring recombinant plasmid pGEX/T1 and pGEX/T1S were induced with 1 mM of IPTG at $OD_{600\ nm}$~0.5 for different times. The bracket indicates the optimum values of every parameter. The total activity was calculated based on 1 L of culture.

Theoretically, expression of T1 lipase as GST fusion protein in prokaryotic system allows rapid purification of recombinant lipase through affinity chromatography. However, we are failed to purify the soluble fraction of recombinant lipase because it did not bind to glutathione Sepharose 4FF even though a high level of activity was detected. It might be due to high hydrophobic region of GST and signal peptide lead to conformation changes and improperly folded of GST domain. In some cases, GST fusion proteins are totally or partly insoluble. Furthermore, high level expression might be contributing to improper folding of partial and highly insoluble fusion protein and subsequently interfere it from binding to affinity column.

According to Frangioni and Neel (1993), the insolubility of GST fusion protein was common. So, Sarkosyl lysis method was used to solubilize partially improper folded active T1 fusion lipase. The non-ionic detergent Triton X-100 was used to sequester sarkosyl with the hope to refold back the solubilized fusion protein in correct folding which subsequently allow GST fusion protein to bind with affinity glutathione Sepharose 4FF. As shown in Table 6, a recovery of around 25% and purification fold of 7.3 was achieved through anionic and non-ionic detergents treatment of fusion protein.

TABLE 6

Purification of GST fusion lipase with signal peptide.

| Purification steps | Total activity (U) | Total protein (mg) | Specific activity (U/mg) | Recovery (%) | Purification fold |
|---|---|---|---|---|---|
| Cell lysate | 1,824.90 | 37.90 | 48.15 | 100.00 | 1.00 |
| Glutathione Sepharose | 454.79 | 1.29 | 352.55 | 24.92 | 7.31 |

Note:
The fusion protein was solubilized with 2% anionic detergent Sarkosyl and 1% non-ionic detergent Triton X-100 for binding to affinity chromatography.

Signal peptide control the entry of all virtually all proteins to the secretory pathway, both in eukaryotes and prokaryotes and cleaved off while the protein is translocated through the membrane. However, it does not contribute to the structural gene of thermostable T1 lipase. Thus, we tried to express the T1 lipase by omitting the signal peptide with the aimed to improve the folding and interaction of GST tag and T1 mature lipase without interfering of the affinity binding of GST fusion protein to immobilized glutathione at matrix support.

Removing of signal peptide rigidify the fusion lipase since a total of 28 amino acid residues limited the movement of T1 lipase in covering the GST moiety. Manipulation of T1 lipase gene significantly improved the expression level by 4.25 and 2.70 fold for induction time and inducer concentration, respectively (Table 1). Further optimization expression encountered an expression level of 41,902 U/L of culture when induced with 0.025 mM of IPTG at $OD_{600nm}$ ~0.75 for 12 hour. It was around 279 fold increased in expression level when compared to wild-type Geobacillus sp. Strain T1.

Figure 2:
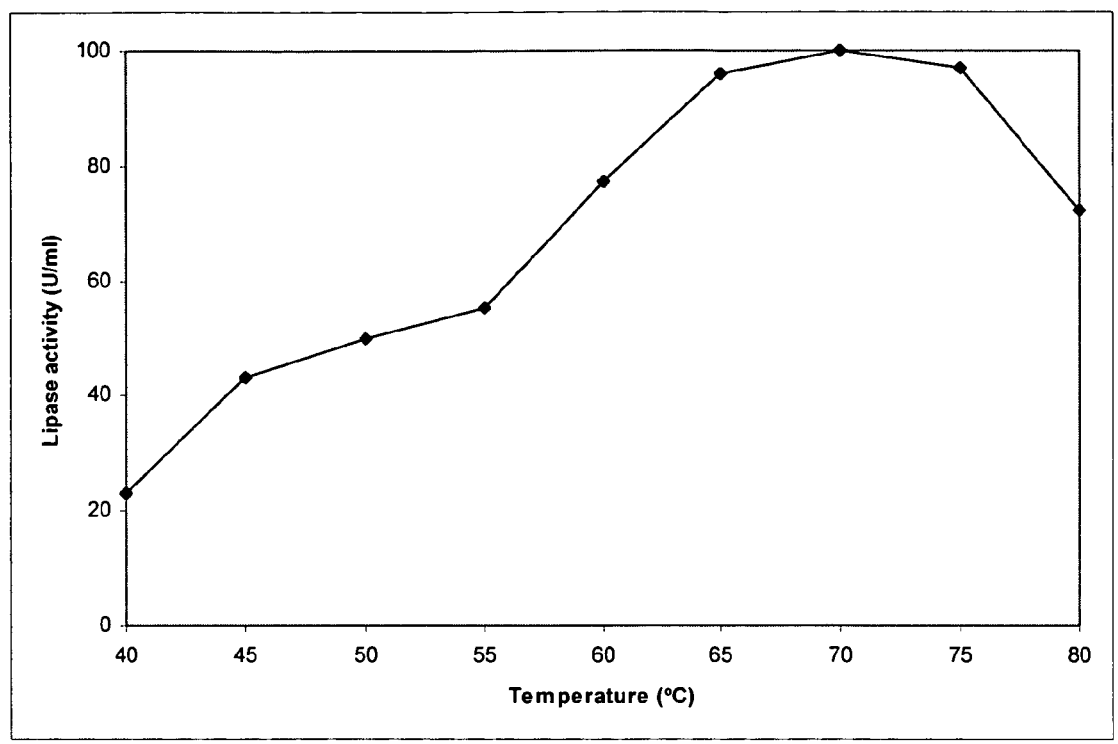
FIG. 2 is a diagram showing temperature activity of T1 mature lipase. Purified T1 lipase was assayed at different temperatures for 30 minute under shaking rate of 250 rpm with olive oil as substrate.

Removing the signal peptide from the fusion protein not only improved the yield of active T1 lipase but also simplifying the purification through affinity chromatography glutathione Sepharose 4FF column to homogeneity (FIG. 2). As shown in Table 7, the recovery obtained was around 72.55% with the purification fold of 2.87. Purification of fusion lipase increased the specific activity from 103.762 U/mg (crude cell lysate) to 297.929 U/mg (purified fusion lipase).

T1 mature lipase was obtained through subsequent purification steps (Table 8). The fusion lipase was cleavage with thrombin protease at 20° C. for 20 hour and subjected to Sephadex G-25 to exchange buffer to PBS (pH 7.3) and remove free glutathione prior to dialysis. It was subjected to affinity chromatography glutathione sepharose HP, HiTrap glutathione sepharose 4FF and Benzamidine FF (high sub) in series to remove the GST tag and thrombin enzyme.

TABLE 7

Purification of GST fusion lipase without signal peptide

| Purification Steps | Total activity (U) | Total protein (mg) | Specific activity (U/mg) | Recovery (%) | Purification fold |
|---|---|---|---|---|---|
| Cell lysate | 3,732.331 | 35.970 | 103.762 | 100.00 | 1.00 |
| Glutathione Sepharose | 2,707.880 | 9.089 | 297.929 | 72.55 | 2.87 |

Notes:
Direct purification of fusion protein was conducted with affinity Glutathione Sepharose 4FF column without any detergent.

TABLE 8

Purification of T1 mature lipase

| Purification Steps | Total activity (U) | Total protein (mg) | Specific activity (U/mg) | Recovery (%) | Purification fold |
|---|---|---|---|---|---|
| Cell lysate | 28,848.120 | 138.255 | 208.659 | 1.00 | 100.00 |
| Affinity 1 | 20,557.051 | 42.038 | 489.011 | 71.26 | 2.34 |
| Affinity 2 | 14,852.742 | 15.487 | 959.033 | 51.49 | 4.60 |

Sepharose HP, HiTrap glutathione Sepharose 4FF and Hitrap Benzamidine (high sub) attached in series.

Characterization of T1 Fusion and Mature Lipase

The T1 lipase was tested at temperatures ranging from 40° C. to 80° C. at 5° C. intervals for 30 min for enzyme activity. The thermostability test was conducted at various temperatures for different hours. Recombinant T1 lipase was also kept at a wide range of pH values ranging from pH 4-12 for pH activity and stability determination. The buffer systems used were 50 mM acetate buffer (pH 4-6), potassium phosphate buffer (pH 6-8), Tris-HCl buffer (pH 8-9), glycine-NaOH buffer (pH 9-11), and $Na_2HPO_3$/NaOH buffer (pH 11-12). The effect of effectors (metal ions, surfactants) and inhibitors were studied at a concentration of 1 mM and 5 mM, respectively at 50° C. for 30 min with an exceptional for pepstatin (1.0 mM).

Figure 3:
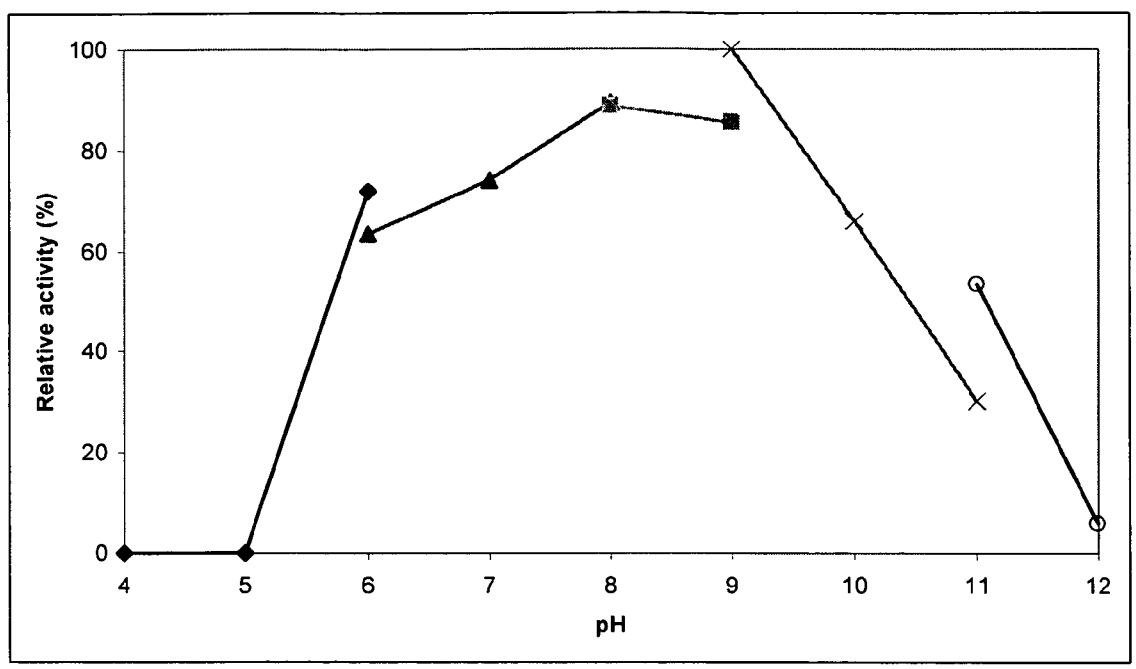
FIG. 3 is a diagram showing activity test of T1 lipase that was assayed at various pH or 30 minute.
Figure 4:
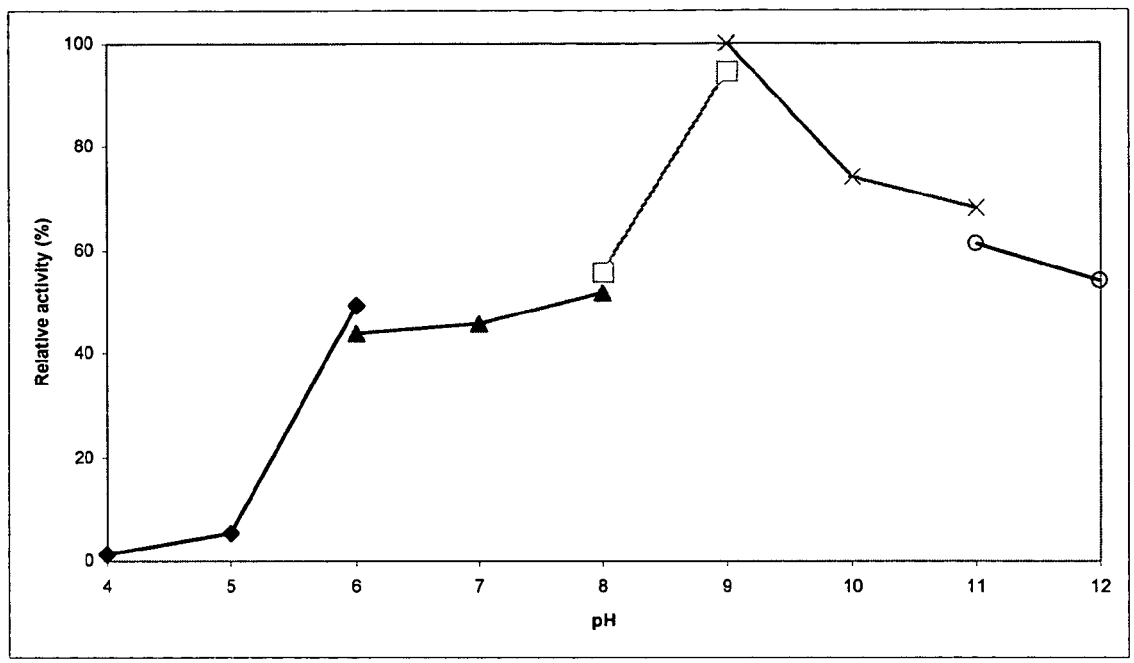
FIG. 4 is a diagram showing stability of T1 lipase that was assayed after pre-treatment with various pH from pH 4 to pH 12 for 30 minute.

The effect of temperature activity and stability was tested at various temperatures for 30 min. It was most active in the temperature range 60° C. to 80° C., with maximal activity at 70° C. (FIG. 2). The effect of pH on activity and stability on lipase activity was conducted at various pHs for 30 min under shaking condition. As shown in FIG. 3, it was active over wide pH range especially pH 6 to 10 with an optimum pH of 9 with olive oil as substrate. pH treatment showed that T1 mature lipase was relatively stable at alkaline pH (FIG. 4).

Figure 5:
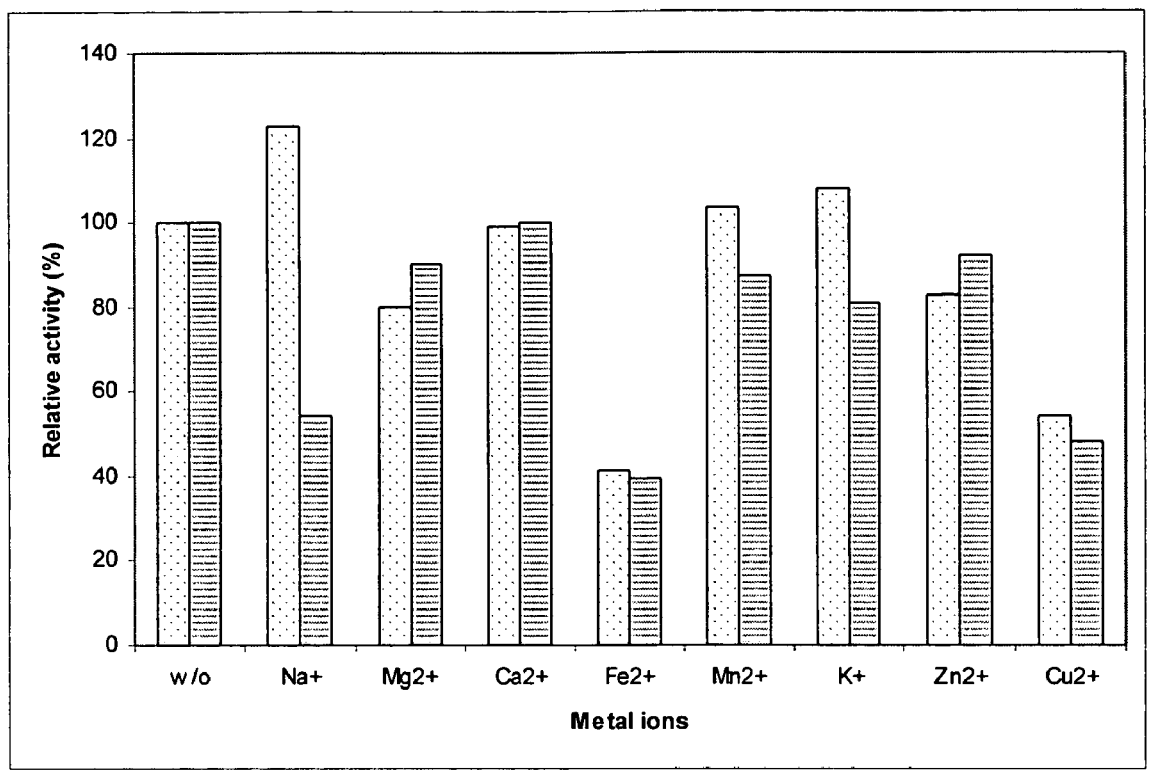
FIG. 5 is a diagram showing effect of metal ions on lipase activity.
Figure 6:
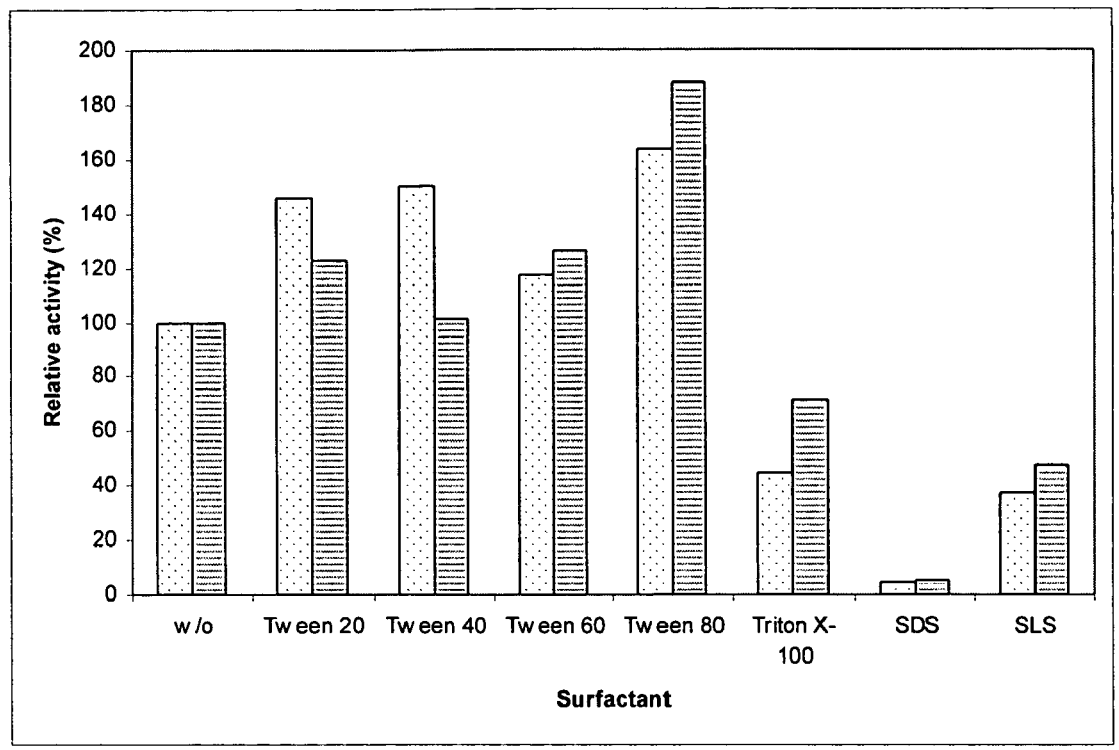
FIG. 6 is a diagram showing effect of surfactants on lipase activity.

The effect of metal ion at final concentration of 1 mM was tested by treatment at 50° C. for 30 min. As shown in FIG. 5, $Na^+$, $Mn^{2+}$ and $K^+$ slightly enhanced the lipase activity after 15 min of treatment. $Mg^{2+}$, $Mn^{2+}$, $Ca^{2+}$, $K^+$ and $Zn^{2+}$ showed stabilizing effect even after 30 min of treatment especially $Ca^{2+}$ without significant lost of enzyme activity. However, $Fe^{2+}$ and $Cu^{2+}$ strongly inhibited the lipase activity by 60% and 52% after 30 min. The effect of surfactants on lipase activity on lipase activity was studied at concentration of 0.1% (FIG. 6). Addition of 0.1% Tween, obvious enhancement was seen especially Tween 80 which increased the lipase activity by 63% and 88% after 0 and 30 min of treatment, respectively.

Figure 7:
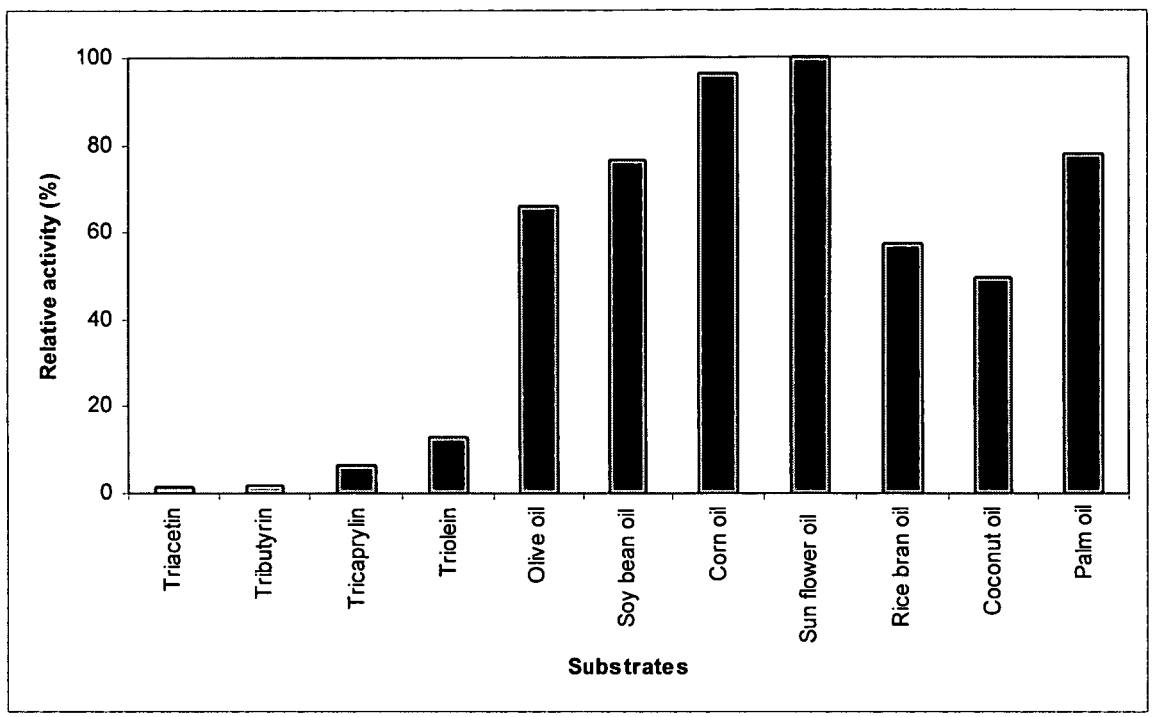
FIG. 7 is a diagram showing effect of substrates on lipase activity.

The effect of substrates on lipase activity of various triglycerides and natural oils were used to study the substrate specificity. FIG. 7 showed that the T1 lipase was preferred natural oils as substrates compared to triglycerides. It more selective to long carbon chain natural oils such as olive oil, corn oil, sunflower oil and palm. This opened the good opportunity for T1 lipase as catalyst in industrial application.

Figure 8:
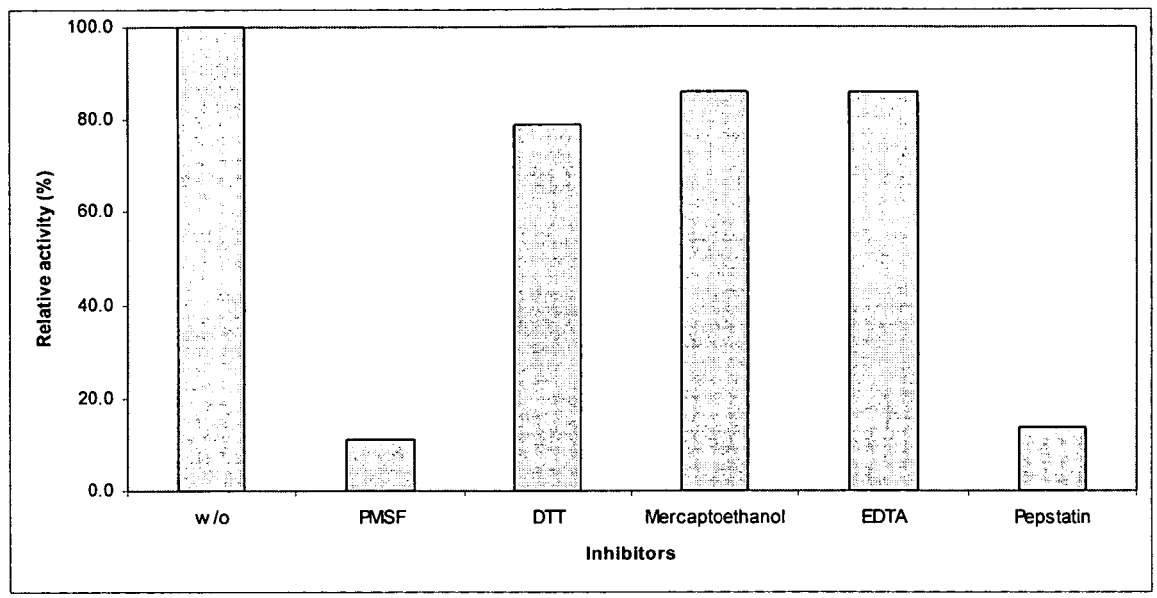
FIG. 8 is a diagram showing effect of inhibitors on lipase activity.

The effect of inhibitors on lipase activity on several metal chelating agent, reducing agents, serine and aspartate inhibitors were used to study the inhibition effect to T1 mature lipase. It was not a metalloenzyme since EDTA showed slightly effect on lipase activity even at 5 mM. The reducing agents such as β-mercaptoethanol and DTT gave little inhibition effect on T1 lipase. The lipase was strongly inhibited by the addition of 5 mM PMSF and 1 mM of Pepstatin, showing that serine and aspartate residues play an important key role in the catalytic mechanism (FIG. 8). The P1 lipase from Bacillus stearothermophilus showed 77% inhibition with the presence of 10 mM of PMSF (Sunchaikul et al., 2001).

The properties of purified T1 fusion and mature lipase were compared to study the effect of GST tag on lipase activity. Both lipases was purified and their physiochemical properties was studied (Table 9). The fusion partner slightly decreased the optimum temperature and pH to 65° C. and pH 8, respectively. There are no significant different was observed with metal ions and substrates. However, Tween 20-80 gave enhancement effect to T1 mature lipase but only stable with the presence of fusion partner. Both of them were inhibited by serine and aspartate inhibitor at tested concentration.

TABLE 9

A comparison of thermostable T1 mature lipase and fusion lipase

| Properties | Fusion lipase | mature lipase |
|---|---|---|
| Optimum temperature | 65° C. | 70° C. |
| Temperature stability | $T_{1/2}$ = 2.5 h at 65° C. | $T_{1/2}$ = 12 h at 60° C. |
| Optimum pH | 8 | 9 |
| pH stability | 8-10 | 8-11 |
| Metal ions | $Mg^{2+}$, $Ca^{2+}$, $Mn^{2+}$, $K^+$ and $Na^+$ | $Mg^{2+}$, $Ca^{2+}$, $Mn^{2+}$, $K^+$ and $Zn^{2+}$ |
| Surfactants | Stable with Tween and Triton X-100 | Stable with Tween and Triton X-100 |
| Substrates | natural oils | natural oils |
| Inhibitors | PMSF and Pepstatin | PMSF and Pepstatin |

Since the GST tag was rigidly fused to T1 mature lipase without signal peptide, so it only conferred a minimal effect on tertiary structure and biological activity without significantly changing of physiochemical properties. There are no significant difference between T1 fusion and mature lipases except the optimum pH and temperature in which only one unit pH and 5° C. higher was encountered for T1 mature lipase. The behavior of T1 fusion and mature lipase to serine and aspartate inhibitors were the same. So, we proposed the T1 lipase fused to GST tag for higher production economically to simplify fusion protein purification for industrial application especially in detergent formulation for warm wash laundry detergent. In addition, the precipitate formed by fusion protein because of aggregation at high concentration of fusion lipase was easily solubilized by resolving it in buffer pH 9 that is far away from the pI of fusion lipase.

We claim:

1. A process for producing a thermostable T1 lipase as a fusion protein that lacks a signal peptide, wherein said process comprises culturing an *Escherichia coli* harboring a recombinant plasmid that comprises a polynucleotide sequence that encodes, as a fusion protein, a thermostable T1 lipase that lacks a signal peptide and glutathione-S-transferase GST, wherein primers of SEQ ID NOS. 2-4 are used for amplification of the open reading frame of the thermostable T1 lipase and its cloning into the recombinant plasmid, wherein the polynucleotide sequence is from a *Geobacillus* Strain T1, and wherein the *Geobacillus* Strain T1 is that which is deposited as *Geobacillus* sp. T1-DSM 17139.

2. The process of claim 1, wherein said polynucleotide sequence is subcloned into any of the following vectors: pBAD, pGEX-4T1, pRSET C, and pET22b(+), and wherein the vector contains any one of the following promoters: araC, T7, T7 lac, and tac promoters.

3. The process of claim 2, wherein the vector is pGEX-4T1, which has a tac promoter that regulates lipase production.

4. The process of claim 1, wherein said fusion protein has a molecular weight of around 63 kDa.

5. The process of claim 1, wherein the step of culturing the *Escherichia coli* harboring the recombinant plasmid(s) comprises inducing the production of the fusion protein with isopropyl-β-D-thiogalactopyranoside (IPTG).

6. The process of claim 5, wherein the *Escherichia coli* harboring the recombinant plasmid(s) is induced with 0.025 mM of IPTG for at least 12 hours; and the process further comprising the step of detecting about 40,000 U of lipase activity from the induced *Escherichia coli*.

7. The process of claim 5, further comprising the step of purifying the fusion protein using affinity chromatography.

8. The process of claim 7, wherein the purification step further comprises subjecting the purified fusion protein to anionic and non-ionic detergent treatment, wherein the purification step recovers between 70% to 75% of the fusion protein that presents a purification fold of 2.8 and/or lipase activity at about 300 U/mg.

9. The process of claim 7, further comprising the step of cleaving off the GST from said purified fusion protein.

* * * * *